US005770778A

United States Patent [19]

Naujokas

[11] Patent Number: 5,770,778

[45] Date of Patent: Jun. 23, 1998

[54] PURIFICATION OF ETHYLENE GLYCOL RECOVERED FROM POLYESTER RESINS

[75] Inventor: Andrius Algimantas Naujokas, Webster, N.Y.

[73] Assignee: Eastman Kodak Company, Rochester, N.Y.

[21] Appl. No.: 678,018

[22] Filed: Jul. 10, 1996

Related U.S. Application Data

[60] Provisional application No. 60/001,631 Jul. 28, 1995.

[51] Int. Cl.[6] .......................... C07C 31/18; C07C 27/26

[52] U.S. Cl. .......................... 568/872; 568/871; 568/852

[58] Field of Search .......................... 568/852, 868, 568/870, 871, 872; 502/415, 416

[56] References Cited

U.S. PATENT DOCUMENTS

| | | | |
|---|---|---|---|
| 3,360,134 | 12/1967 | Pullen | 210/502 |
| 3,398,061 | 8/1968 | Taul et al. | 203/18 |
| 3,625,886 | 12/1971 | Mattia et al. . | |
| 4,795,735 | 1/1989 | Liu et al. | 502/415 |
| 4,855,276 | 8/1989 | Osborne et al. | 502/415 |
| 4,923,843 | 5/1990 | Saforo . | |
| 5,051,528 | 9/1991 | Naujokas et al. | 560/78 |
| 5,298,530 | 3/1994 | Gamble et al. | 521/48.5 |
| 5,393,916 | 2/1995 | Gamble et al. | 560/78 |
| 5,414,022 | 5/1995 | Toot . | |

*Primary Examiner*—Gary Geist
*Assistant Examiner*—Karl J. Puttlitz, Jr.
*Attorney, Agent, or Firm*—Arthur H. Rosenstein

[57] ABSTRACT

There is described a process for purifying ethylene glycol recovered from scrap polyester by contacting the recovered ethylene glycol with, in either order, a first adsorbent that has a high affinity for polar contaminants and a second adsorbent that has a high affinity for non-polar contaminants.

10 Claims, 3 Drawing Sheets

SEPARATION DEVICE
DISTILLATION COLUMN
DISTILLATION COLUMN
FILTER APPARATUS
32
54
50
62
56
46
64
58
66
48
60
68

PURIFICATION OF ETHYLENE GLYCOL RECOVERED FROM POLYESTER RESINS

CROSS REFERENCE TO RELATED APPLICATION

Reference is made to and priority claimed from U.S. Provisional application Ser. No. US 60/001,631, filed 28 Jul. 1995, entitled PURIFICATION OF ETHYLENE GLYCOL RECOVERED FROM POLYESTER RESINS.

FIELD OF INVENTION

This invention relates to purification of ethylene glycol. In a particular aspect, it relates to purification of ethylene glycol that has been recovered from condensation-type polyester resins such as polyethylene terephthalate.

BACKGROUND OF THE INVENTION

Polyester resins have found widespread use in varied applications. Polyester resins, such as polyethylene terephthalate, are used in films, including photographic film, in fibers, and in food and beverage containers. Various methods have been disclosed for the depolymerization of such resins into their component monomers, such as ethylene glycol and terephthalic acid, or derivatives thereof, so that they could be reused.

Naujokas et al. U.S. Pat. No. 5,051,528 describes a process of recovering ethylene glycol and dimethyl terephthalate from polyethylene terephthalate scrap resins by dissolving the polyester resin in oligomers of the same monomers as present in the polyester, passing super-heated methanol through the solution and recovering ethylene glycol and dimethyl terephthalate.

Gamble et al. U.S. Pat. No. 5,298,530, issued Mar. 29, 1994 describes improvements in this process. In this improvement the scrap resin is combined with reactor melt in a dissolver to form a dissolver melt which is transferred to the reactor for contact with super-heated methanol. In the reactor, polymers and oligomers are further depolymerized into component glycol and ester monomers, which are then recovered.

Further improvements and variations in this process are described in Gamble et al. U.S. Pat. No. 5,393,916 issued Feb. 28, 1995, and in Toot et al. U.S. Pat. No. 5,414,022 issued May 9, 1995.

The processes described in these patents reverse the polymerization reaction by which the polyethylene terephthalate is formed by depolymerizing polyethylene terephthalate to dimethyl terephthalate and ethylene glycol. Ethylene glycol recovered in this way contains contaminants that must be removed before it can be reused. Contaminants can be degradation products formed in the recovery process or compounds that were present in the scrap polyester which were not removed during the recovery process.

Ethylene glycol recovered from scrap polyester usually is purified by distillation. However, contaminants found with ethylene glycol have a wide range of volatilities, polarities and molecular weights. Some are more volatile than ethylene glycol, while others are less volatile. Thus, continuous distillation using a single column normally may not be sufficient to obtain ethylene glycol of a desired purity. Therefore, an additional purification step, such as treatment with an adsorbent, frequently is employed. U.S. Pat. No. 3,398,061 describes the use of an acid activated clay for this purpose. Activate carbon is another adsorbents that have been used for this purpose.

I have found that the useful life of activated carbon adsorbent used to purify ethylene glycol recovered from scrap polyester can vary over a wide range. I have further found that this depends not only on the amount of the contaminants removed, but also on the properties of the contaminants. Still further, I have found that the properties of the contaminants can vary depending upon the scrap used in the recovery process and the conditions under which the recovery process is run.

It would be desirable to have a process by which ethylene glycol of a desired purity is recovered while increasing the useful life of the filtration material used to purify it.

SUMMARY OF THE INVENTION

I have found that if two different types of adsorbent are employed, the useful life of the filter is dramatically increased. Thus, the present invention provides a process for purifying ethylene glycol recovered from scrap polyester by contacting the recovered ethylene glycol with, in either order, a) a first adsorbent that has a high affinity for polar contaminants, and b) a second adsorbent that has a high affinity for non-polar contaminants.

Individual adsorbents having high affinity for polar or non-polar material are known, as are composite adsorbents that have an affinity for both types of materials. The latter are described in, for example, U.S. Pat. Nos. 3,360,134, 4,795,735, 4,855,276 and 4,923,843. However, it has not, heretofore, been recognized that ethylene glycol recovered from scrap polyester had two different types of contaminants, nor that these contaminants could simply and effectively be removed by the use of two distinctly different types of adsorbents.

The present invention provides a simple, economic means for purifying ethylene glycol recovered from scrap polyester.

DETAILED DESCRIPTION OF THE INVENTION

In its broadest aspects, the present invention can be applied to ethylene glycol from whatever source obtained. In a preferred embodiment, the present invention is applied to ethylene glycol obtained from the apparatus and process depicted in FIGS. 1 and 2, and can be either a batch process or a continuous process applied to the output of the distillation column (58) in FIG. 2.

Figure 1:
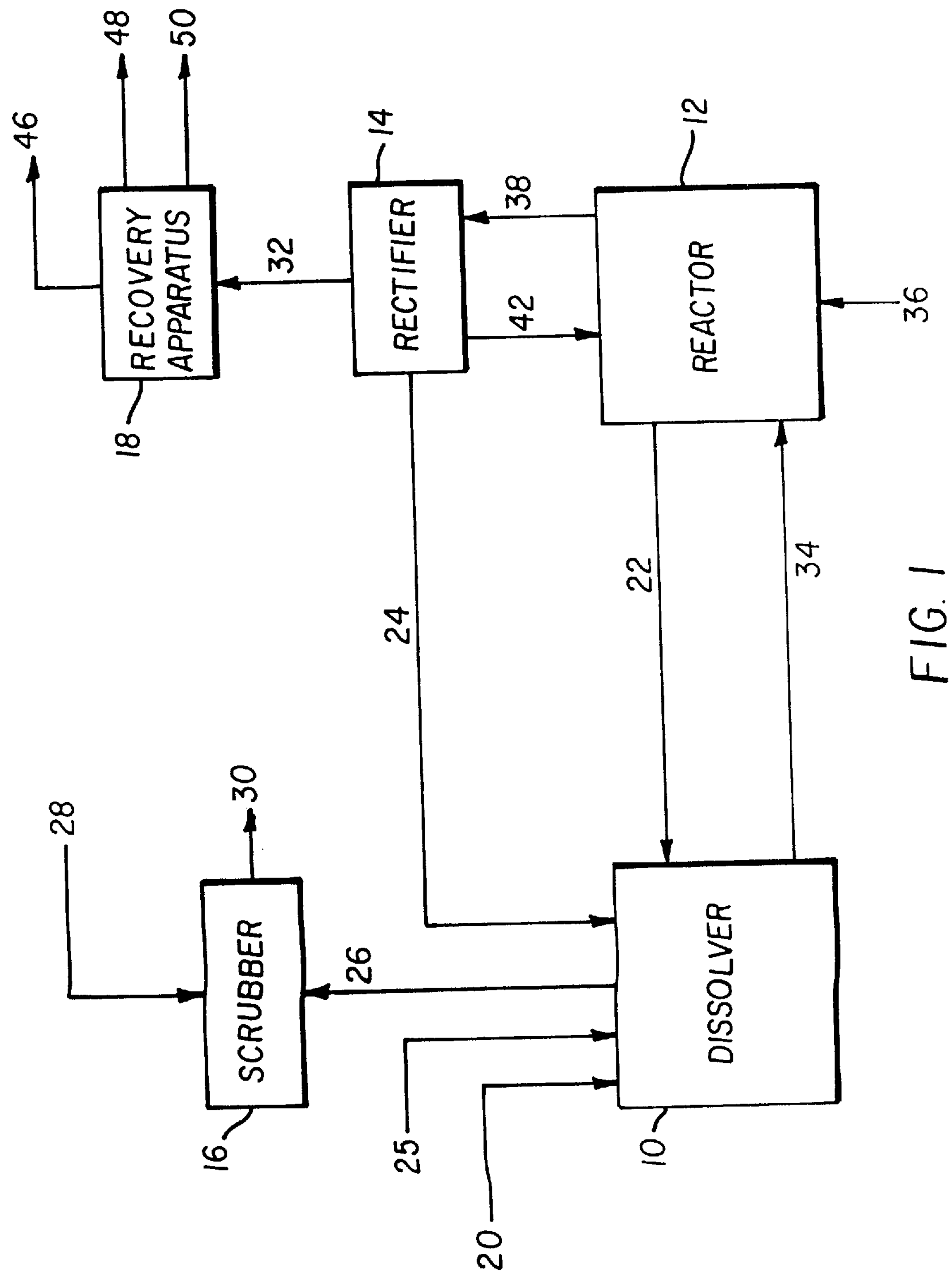
FIG. 1 is a schematic flow diagram illustrating preferred depolymerization apparatus to obtain ethylene glycol which can be purified in accordance with this invention.

The apparatus of FIG. 1. comprises:

a dissolver for receiving polyester, a reactor for depolymerizing polyester into monomer components, and a rectifier for separating monomer components.

This apparatus is used in a process which comprises the steps of:

a) adding polyester to the dissolver and combining it with melt from the reactor to reduce the chain length of the polyester, b) transferring reduced chain length polyester from the dissolver to the reactor, c) passing super-heated methanol through the reactor to depolymerize polyester into its constituent monomers, d) transferring depolymerization products from the reactor to the rectifier;

e) separating the depolymerization products in the rectifier into a vapor phase containing monomer components and a liquid phase containing higher molecular weight materials; and f) recovering ethylene glycol exiting the rectifier, g) purifying the ethylene glycol recovered in step f) by distillation, and h) further purifying the ethylene glycol from step g) by contacting it with, in either order, i) a first adsorbent that has a high affinity for polar contaminants and ii) a second adsorbent that has a high affinity for non-polar contaminants.

In the apparatus of FIG. 1 a dissolver (10), a reactor (12), and a rectifier (14), are connected by the pipes, pumps and valves to transfer the materials in accordance with the process of the invention. Optionally included in this apparatus are a scrubber (16), for recovering gases from the dissolver.

In practice, polyethylene terephthalate (20) in a suitable form and size is introduced into the dissolver by any suitable means where it is liquefied and reduced in chain length. The dissolver can be run at atmospheric pressure. Thus, simple solids handling devices such as rotary air locks can be employed to introduce the polyester resin. Suitable means for introducing the polyester include an air conveyor, a screw feeder, an extruder, and the like.

The dissolver is equipped with means for heating its contents to a temperature of up to about 305° C. In practice the dissolver is maintained at a temperature in the range of 240° to 260° C.

One or both of the reactor melt (22) and the rectifier liquid (24) can be introduced into the dissolver via suitable piping. Valves can be placed in their flow path to control the rate of introduction of these materials and their relative proportions. The reactor and rectifier are run at a higher pressure than the dissolver, thus eliminating the need for pumping means to transfer reactor melt and rectifier liquid to the dissolver, although pumping means can be employed, if desired.

Reactor melt and rectifier liquid introduced into the dissolver react with the polyester to shorten the average chain length. This initiates the depolymerization reaction and decreases the viscosity of the dissolver contents. In addition, there can be added to the dissolver an ester exchange catalyst (25), such as zinc acetate. Such catalysts are known in the art to facilitate the depolymerization process. The catalyst can be employed in a range of 0 to 800 parts by weight per million parts by weight of solid polyester introduced into the dissolver. Preferably the catalyst is employed in the range of 30 to 300 ppm polyester, and most preferably the catalyst is employed in the range of 30 to 100 ppm polyester.

In a preferred embodiment, the melt in the dissolver is protected from the atmosphere by a blanket of nitrogen. This reduces degradation of the dissolver melt due to oxidation reactions.

The reactor melt and dissolver melt comprise methanol, low molecular weight polyesters, monomers, monohydric alcohol-ended oligomers, glycols, dimethyl terephthalate and methylhydroxyethyl terephthalate. The major difference between these two melts is the average chain length of the polyester. The rectifier liquid contains the same components except for polyesters.

The viscosity of the dissolver melt preferably is maintained in the range of 0.002 to 0.1 Pa.s. This is sufficiently low to permit the use of inexpensive pumping and heating means, and permits the reactor to be operated at optimum pressures to provide good yields of monomer. The flow rates of material in and out of the dissolver can be adjusted to maintain the viscosity at the desired level.

The dissolver also can be equipped with means for removing contaminants that are introduced with the polyester. Most contaminants are removed from the melt in the dissolver before introduction of the dissolver melt to reactor. Inorganic contaminants such as metals or sand are removed by a filter. Polyolefins and other contaminants that float on top of the dissolver melt are drawn off.

The gases (26) which evolve in the dissolver contain monomers that preferably are recovered together with the monomers exiting the reactor. This can be accomplished by passing the gases to the scrubber where they are treated with and absorbed by liquid methanol (28). This material (30) can then be passed to separation apparatus (18) where it can be combined with material (32) exiting the rectifier.

Melt (34) from the dissolver is transferred to the reactor by suitable piping and pumps. Superheated methanol vapor (36) is provided to the reactor by conventional means. The methanol introduced into the reactor heats the reactor contents and acts as a depolymerization agent. The effectiveness of the super-heated methanol for heating the reactor contents and for stripping gases depends on its volumetric flow rate; the depolymerization rate in the reactor therefore is a function of the methanol flow rate to the reactor. Methanol is introduced into the reactor at a rate in the range of 2 to 6 parts by weight methanol per part polyester.

There is transferred from the reactor to the rectifier a vapor stream (38) comprising methanol, glycols including ethylene glycol, diethylene glycol, and triethylene glycol, dimethyl terephthalate, dimethyl isophthalate, cyclohexanedimethanol, and methylhydroxyethyl terephthalate. The rectifier separates methylhydroxyethyl terephthalate from the vapor stream exiting the reactor and can return all or part of it to the dissolver in the form of a liquid (24) together with dimethyl terephthalate, glycols and methanol. Excess liquid (42) from the rectifier drains back into the reactor.

Figure 2:
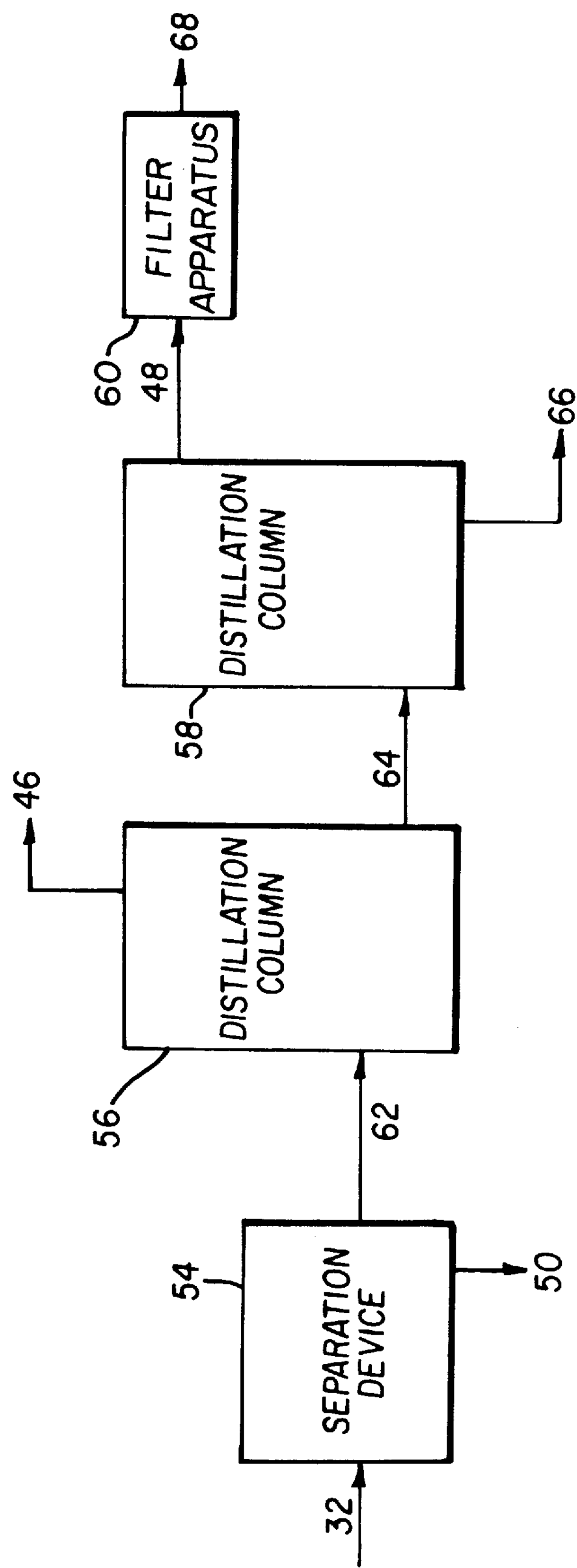
FIG. 2 is a schematic flow diagram of a recovery apparatus with which the present invention can be used.

The remainder of the vapor stream (32) is transferred from the rectifier to separation apparatus (18), which is shown in greater detail in FIG. 2., where methanol (46) is recovered for further use, and the glycol components (48) separated from the terephthalate components (50).

As shown in FIG. 2, the output (32) from the rectifier, after removal of excess methanol, is sent to a separation device (54), such as a crystallizer, where dimethyl terephthalate (50) is recovered and further methanol is removed. The residue (62) contains methanol, ethylene glycol, higher glycols, residual dimethyl terephthalate, other terephthalates and oligomers. Methanol (46) is separated in a first distillation operation using a distillation column (56). Higher boiling components (64) are transferred to a second distillation column (58) in which the ethylene glycol (48) is separated from waste (66). The ethylene glycol output of this distillation column is passed through filter apparatus (60) comprising one or more beds of adsorber material from which purified ethylene glycol (68) is recovered.

The filter apparatus can comprise one or more filter beds containing adsorbent media. If one bed is employed, it should contain a mixture of a filter media that has a high affinity for polar contaminants and a filter media that has a high affinity for non-polar contaminants. If more than one filter bed is employed, they can contain mixed filter media, as is used in the single bed, each bed can contain a single type of filter media, as long as beds containing each of the two types are employed, or there can be combinations of these two type of beds.

The adsorbents that have a high affinity for polar contaminants include activated alumina, molecular sieves, silica gel, and the like. Representative examples of such adsorbents are sold under such tradenames as Linde Molecular Sieves, Alcoa F200, F1, CPN and F6 Alumina, Norton Alumina, Discovery Alumina.

The adsorbents that have a high affinity for non-polar contaminants are activated carbon, hydrophobic molecular sieves, activated carbon molecular sieves, and the like. Representative examples of such adsorbents are sold under such tradenames as Carborundum GAC 40 Carbon, Calgon SGL Carbon.

The two different types of adsorbents are used in proportions in the range of 1 part by weight adsorbent that has a high affinity for polar contaminants to from 1 to 10 parts by weight adsorbents that have a high affinity for non-polar contaminants.

The flow rate of ethylene glycol through the filter bed or beds is not critical, and can be in the same range as that used in a single adsorbent system, and should be consistent with the recommendations of the manufacturer of the adsorbent material.

The purity of the resulting ethylene glycol can be determined in a number of ways, a convenient way is to measure purity by a heat stress color determination.

EXAMPLES

The following examples illustrate the invention. Unless otherwise indicate, all parts are by weight.

All experiments measured the dynamic adsorption of contaminants in ethylene glycol that has been recovered from scrap polyester by a process like that described in connection with FIGS. 1 and 2. The experimental apparatus comprised a jacketed glass column having a length of about 1 m. and an internal diameter of about 2.5 cm. The desired temperature was maintained in the column by running hot water through the jacket. Adsorbent media was added to the column and ethylene glycol was pumped through the column using a variable rate metering pump. There was a sampling point at the exit of the column.

In dynamic adsorption, where a fluid is passed through a bed of an adsorbent, mass transfer effects as well as adsorptive properties determine the efficiency of separation of impurities. When the adsorbent capacity is used up, the concentration of the impurity in the effluent stream rapidly increases. This is referred to as "column breakthrough."

Purity of the ethylene glycol was determined by measuring "four-hour heat color." This is determined by a) spectrophotometrically measuring the optical density in the wavelength range from 400 to 500 nm. of a sample of ethylene glycol, b) incubating the sample for four hours at a temperature of 180° C., c) spectrophotometrically measuring the optical density of the incubated sample in the wavelength range from 400 to 500 nm., and then d) calculating the increase in optical density.

Example 1

This illustrates the conditions in existence prior to this invention.

Figure 3:
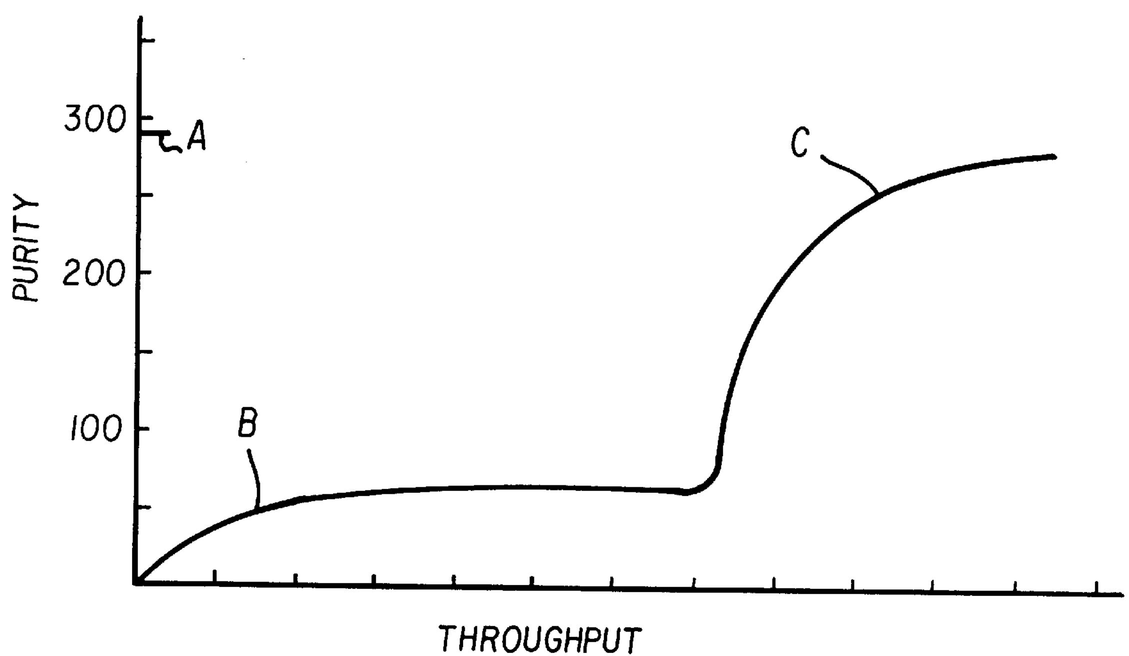
FIGS. 3 and 4 are plots of throughput vs. color of purified ethylene glycol.

Recovered ethylene glycol, having a four hour heat color at point A in FIG. 3, was passed through a bed of activated carbon to complete breakthrough, i.e., until the inlet and outlet color of the ethylene glycol were the same when subjected to a four hour heat color test. A bimodal breakthrough curve was observed. The first breakthrough occurring at point B in FIG. 3 and the second breakthrough occurring at point C in FIG. 3. It was postulated that this bimodal curve evidenced the presence of at least two different types of contaminants. The first breakthrough occurring when the bed becomes saturated with contaminants that have a low affinity for activated carbon; and the second breakthrough occurring when the bed becomes saturated with contaminants that have a higher affinity for activated carbon.

Example 2

This illustrates the present invention.

Figure 4:
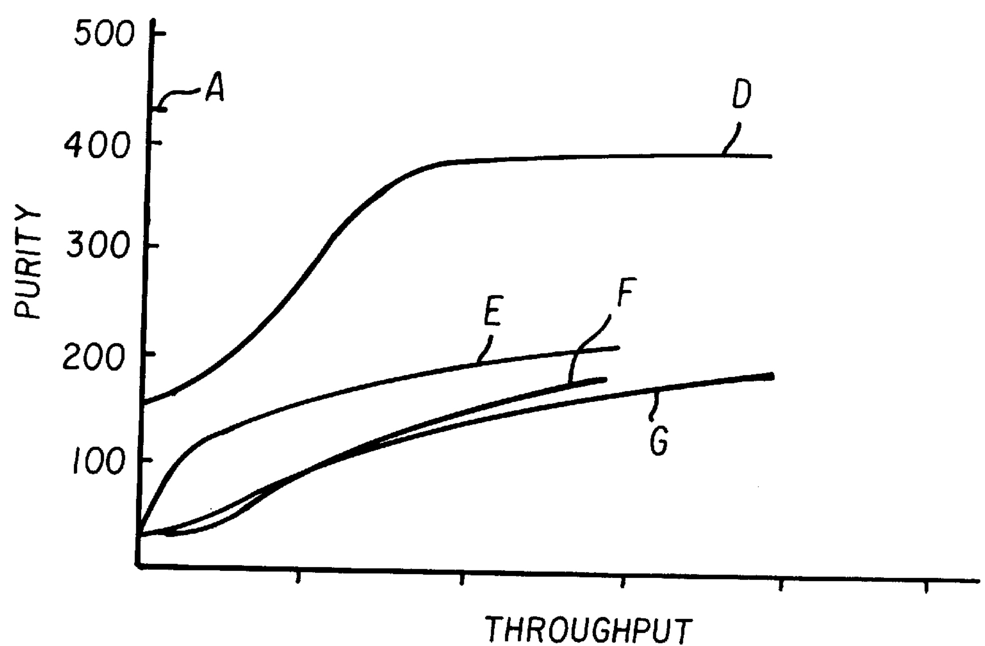

Example 1 was repeated using four different combinations of adsorbent media. In each test the total amount of adsorbent media was the same. The adsorbent media used were as follows: D) all activated alumina, E) all activated carbon, F) equal amounts of activated carbon followed by activated alumina, and, finally, G) equal amounts of activated alumina followed by activated carbon. FIG. 4 shows breakthrough curves for these four beds. It is observed that the beds with the two different adsorbents have significantly longer life than either of the beds with only a single adsorbent.

The invention has been described by reference to preferred embodiments, but it will be understood changes can be made to the apparatus and process steps specifically described herein within the spirit and scope of the invention.

What is claimed is:

1. A process for purifying ethylene glycol recovered from scrap polyester by contacting the recovered liquid ethylene glycol with, in either order, a) a first adsorbent that has a high affinity for polar contaminants, and b) a second adsorbent that has a high affinity for non-polar contaminants.

2. A process of claim 1, wherein the first adsorbent is activated alumina.

3. A process of claim 1, wherein the second adsorbent is activated carbon.

4. A process of claim 1, wherein the ethylene glycol is contacted first with the first adsorbent and then with the second adsorbent.

5. A process of claim 1, wherein the ethylene glycol is contacted first with the second adsorbent and then with the first adsorbent.

6. A process of claim 1, wherein the ethylene glycol is contacted with the first adsorbent and the second adsorbent at the same time.

7. A process of claim 1, wherein the first and second adsorbents are present in a ratio of 1:1 to 1:10 parts by weight.

8. A process for recovering and purifying liquid ethylene glycol from polyester resins using apparatus that comprises:

a dissolver for receiving polyester, a reactor for depolymerizing polyester into monomer components, and a rectifier for separating monomer components;

the process comprising a) adding polyester to the dissolver and combining it with melt from the reactor to reduce the chain length of the polyester, b) transferring reduced chain length polyester from the dissolver to the reactor, c) passing super-heated methanol through the reactor to depolymerize polyester into its constituent monomers, d) transferring depolymerization products from the reactor to the rectifier;

e) separating the depolymerization products in the rectifier into a vapor phase containing monomer components and a liquid phase containing higher molecular weight materials;

f) recovering ethylene glycol exiting the rectifier, g) purifying the ethylene glycol recovered in step f) by distillation, and h) further purifying the ethylene glycol purified in step g) by contacting it with, in either order, i) a first adsorbent that has a high affinity for polar contaminants, and ii) a second adsorbent that has a high affinity for non-polar contaminants.

9. A process of claim 8, wherein the first adsorbent is activated alumina and the second adsorbent is activated carbon.

10. A process of claim 9, wherein the first and second adsorbents are present in a ratio of 1:1 to 1:10 parts by weight.

* * * * *